United States Patent [19]
Dollinger et al.

[11] Patent Number: 5,269,937
[45] Date of Patent: Dec. 14, 1993

[54] HPLC LIGHT SCATTERING DETECTOR FOR BIOPOLYMERS

[75] Inventors: Gavin D. Dollinger, San Francisco; Robert L. Cunico, Hercules; Michael G. Kunitani, San Rafael, all of Calif.

[73] Assignee: Cetus Corporation, Emeryville, Calif.

[21] Appl. No.: 601,840

[22] Filed: Oct. 23, 1990

[51] Int. Cl.⁵ ............................................. B01D 15/08
[52] U.S. Cl. ...................... 210/656; 210/85; 210/198.2; 204/180.1; 204/299 R; 356/366; 356/368; 356/369; 422/69; 422/70; 436/161; 436/171; 436/177
[58] Field of Search ............ 210/656, 85, 198.2; 204/180.1, 299 R; 422/69, 70; 436/161, 171, 177; 356/366, 368, 369

[56] References Cited
U.S. PATENT DOCUMENTS

| | | | |
|---|---|---|---|
| 4,305,925 | 12/1981 | Kapmeyer | 356/339 |
| 4,313,929 | 2/1982 | Morita | 356/339 |
| 4,535,241 | 8/1985 | Eberhardt | 356/339 |
| 4,796,995 | 1/1989 | Salzman | 356/338 |
| 4,915,501 | 4/1990 | Steen | 356/338 |
| 4,927,268 | 5/1990 | Carr | 356/338 |
| 4,934,811 | 6/1990 | Watts et al. | 356/73 |
| 4,971,441 | 11/1990 | Damlin | 356/338 |

OTHER PUBLICATIONS

Trac: Trends in Analytical Chemistry, vol. 8, No. 7, Aug. 1, 1989, Amsterdam, pp. 260-268; I. Krull et al.: 'Biopolymer Determinations'.
Journal of Applied Polymer Science Applied Polymer Symposium, vol. 43, Oct. 1, 1989, pp. 99-114; C. Jackson et al.: 'Characterization of Biopolymers Using a Multi-Angle Light Scattering Detector'.
Analytical Chemistry, vol. 53, No. 9, Aug. 1, 1981, pp. 1298-1302; J. Jorgenson et al.,: 'Zone Electrophoresis'.
American Laboratory, May 1, 1988, pp. 86-91; P. Wyatt et al.,: 'Absolute GPC Determinations of Molecular Weights'.
Analytical Chemistry, vol. 60, No. 17, Sep. 1, 1988, pp. 1832-1834; W. Kuhr et al.: 'Indirect Fluorescence Detection'.
Stuting et al., 1989, LC-GC 7(5):402417.
Putzeys and Brosteaux, 1935, Trans Faraday Soc. 31:1314-1325.
Heirwegh et al., 1987, J. Biochemical and Biophysical Methods 14:303-322.
Suting and Krull, 1990, Anal. Chem. 62:2107-2114.
Takagi, 1990, J. Chromatography 506:409-416.

*Primary Examiner*—Ernest G. Therkorn

[57] ABSTRACT

A high angle light scattering detector using classical Rayleigh scattering. A high intensity arc light source, filtered to leave only one wavelength illuminates a flow cell. Through the flow cell, very small particles such as biological proteins flow in solution after separation by HPLC or some other means. A UV detector generates data regarding the weight concentration of the eluting particles and a scattered light detector collecting scattered light at angles of approximately 90° generates a scattered light signal. The incident light intensity is also measured. The average molecular weight is then computed using the scattered and incident light data the weight concentration data and a simplified mathematical relationship from which the size factor P and the viral coefficients have been eliminated.

18 Claims, 7 Drawing Sheets

HPLC LIGHT SCATTERING DETECTOR FOR BIOPOLYMERS

BACKGROUND OF THE INVENTION

The invention pertains to the field of characterization and analysis of any material between 2 and 10,000 kilodaltons in molecular weight especially biopolymers or other polymers using classical light scattering. More particularly, the invention pertains to an improvement over classical low angle light scattering detectors and multiangle classical light scattering detectors designed to determine molecular weight of particles emerging from a separation device such as a liquid chromatography column.

The molecular weight of a particle eluting from a liquid chromatography column or other separation process is a very useful thing to know for both characterization of the particle, analysis of the chromatogram and for process monitoring and control. For example, suppose a biological process generates a sample having several different biological proteins of interest and scientists want to separate and identify them by molecular weight for further experiments regarding their utility in treatment of disease or for diagnostic purposes. There are no liquid chromatography columns that separate proteins by molecular weight, but there are columns that separate particles by size. However, size is poor indicator of molecular weight because a biological protein in the natural globular form and the same protein in the denatured state have vastly different sizes but the same molecular weight. It would be useful for separation of the various proteins as they elute from a liquid chromatography column based upon, for example, size, to know the molecular weight of the proteins that cause each peak in the chromatograph. The molecular weight signal can then be used to control a collection system into which the protein stream flows such that the different proteins are captured in different containers.

Some detectors exist in the prior art which detect the difference in refractive index of the output stream of a liquid chromatography column. However, refractive index is not a good indicator of molecular weight because.

Another application where knowledge of the molecular weight of the particles eluting from a liquid chromatography (hereafter LC) column is analysis of chromatograms. In some situations, peaks in a chromatogram generated using a ultraviolet detector (hereafter UV) cannot be deciphered in terms of what types of particles caused the peaks. If a classical light scattering detector is used to generate another chromatogram, the two chromatograms may be compared and the differences between the mass of particles which caused the different peaks in the UV chromatogram may be easily determined.

In the prior art, molecular weight determinations have been difficult and based upon instruments that were designed in 1970 based upon a view of the mathematics of classical light scattering which is not optimized for small particles having sizes less than $\lambda/4$ where $\lambda$ is the incident light wavelength such as biopolymers. Specifically, there is a relationship which mathematically relates molecular weight, Rayleigh scattering, weight concentration of the particles causing the scattering, a size factor called P and another physical characteristic called the second viral coefficient which pertains to the volume excluded by a particular biological protein based upon its characteristics. This second viral coefficient, A, if large, means that a particular biological protein excludes other proteins from a very large volume around it. If A is negative, it means that this biological protein tends to attract other proteins and form agglomerations. More specifically, the relationship is:

$$\frac{KC}{R} = \frac{1}{M_w P(\theta)} + 2A_2 C + 3A_3 C^2 \qquad (1)$$

where

K = an optical constant relating wavelength, refractive index of the solution and change in refraction index of the solution over time among other things and which can be measured empirically for any given system, R = the "specific Rayleigh constant" or the "specific Rayleigh ratio", $\overline{M}_w$ = the weight averaged molecular mass of the scatterers, $P(\theta)$ = a size parameter which corrects equation (1) for the effects of multiple intra-particle scattering, $A_2$ and $A_3$ = the second and third viral coefficients, respectively, and C = the weight concentration of the scattering particles (hereafter the scatterers).

One of the difficulties faced by workers in the art lies in the P factor in equation (1). Specifically, P is given by:

$$P(\theta)^{-1} = 1 + \frac{16\pi^2 n^2 R_g^2 \sin^2 \theta/2}{3 \lambda_o^2} \qquad (2)$$

where $P(\theta)^{-1}$ = the size factor inverse n = the index of refraction $R_g$ = the radius of gyration of the scatterer;

$\theta$ = the scattering angle, i.e., the angle between the incident light and the scattered light, $\lambda$. = the wavelength of the incident light.

Workers in the art of instrument design for instruments that could determine molecular weight worried that because the radius of gyration of the scatterer could not be easily measured and is not known in advance, the size factor P would not be known and could not be ignored without creating an error unless the scattering angle was very small which would make the size factor approximately 1 in equations (1) and (2). As a result, a design evolved in approximately 1970 for an instrument to measure molecular weight which was based upon low light scattering angles such that P could be ignored. Actually $R_g$ can be measured, but it requires a measurement of R (Raleigh scattering) at each of a plurality of angles $\theta$. $\overline{M}_w$ (hereafter the weight averaged molecular mass $\overline{M}_w$ may sometimes be symbolized as simply $M_w$) and $R_g$ can be derived from these measurements. Another instrument design in the prior art used this approach. For low angles $\theta$, $R_g$ need not be known.

Figure 1:
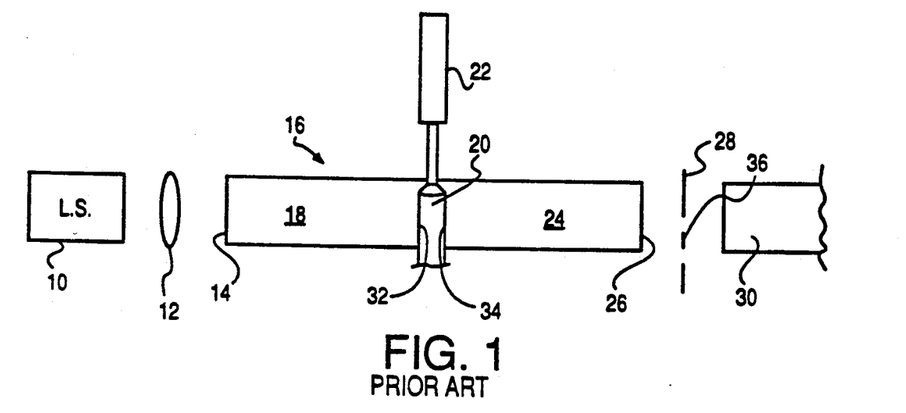
FIG. 1 is a block diagram of a typical prior art low angle scattered light detector.

FIG. 1 is illustrative of this prior art design for a low angle light scattering detector (hereafter LAL) where $R_g$ need not be known. A light source 10 which can be an arc source or a laser generates incident light which is focussed by optics 12 on the input window 14 of a flow cell 16. The flow cell is comprised of a long piece of input glass 18, a scattering volume 20 through which the scatterers eluting from a liquid chromatography column 22 flow in solution, a long piece of output glass 24, an output window 26, a mask 28 and a scattered light detector 30.

Figure 2:
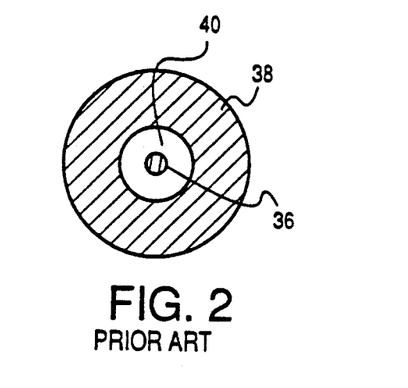
FIG. 2 is an elevation view of the mask 28 in FIG. 1.

The LAL detector of FIG. 1 has many areas in which improvement can be made. First, the signal-to-noise ratio is not optimal in this design for several reasons. The light source 10, if an arc, generates light which is not well collimated and which must be focussed by the optics 12. As the light passes through the optics and enters the input window 14, the imperfections in the lenses and window cause some scattering of the incident light which, if it gets into the detector 30 represents noise since it is not light scattered by the scatterers but light scattered by the machine itself. Further, as the light its the glass 18 and enters the scattering volume 20 and then re-enters glass 24 there is further scattering at the liquid-glass interfaces 32 and 34 caused by imperfections in the glass. Further scattering occurs at the output window 26 caused by imperfections in the glass there. All this scattered light is noise and not data and steps must be taken to eliminate it. One of these steps is to make the glasses 18 and 24 very long such that light scattered at the input window 14, and the interfaces 32 and 34 fairly far away from the detector 30 such that light scattered at these locations misses the detector. Light scattered at the output window 26 is somewhat masked from the detector 30 by the mask 28. FIG. 2 shows the prior art mask configuration for mask 28. The mask is comprised of an opaque center section 36 which blocks nonscattered incident light that passes straight through the flow cell and scattering volume without being scattered from entering the detector 30. The mask also has a concentric opaque outer section 38 which masks off high angle scattered light from entering the detector 30. The region 40 which is not cross-hatched is transparent and allows low angle scattered light to enter the detector regardless of whether it was scattered from the scatterers or by other things such as imperfections in the glass.

It is troublesome to use the structure of FIG. 1 because the flow cell must be disassembled and cleaned ultrasonically or otherwise, almost everyday to prevent dirt from collecting on the various surfaces in the optical path which could cause further scattering.

Further, the design of the optics 12 to focus the arc light is somewhat complicated and expensive if scattered light is to be minimized. With the advent of lasers, the problems of design of the optical system are lessened because lasers output collimated light. However, some optics must be present to "clean up" the laser beam to eliminate some scattered light. The problems of making the windows 14 and 26 and the interfaces 32 and 34 as perfect as possible are also quite difficult.

Another problem with the structure of FIG. 1 is that the output frequency of lasers that are relatively inexpensive (Helium-Neon lasers) is too far into the red end of the spectrum to make a good match for the band of highest sensitivity of the detector 30. Typically, the detector 30 is a photomultiplier tube (hereafter PMT) which has a sensitivity which three times as efficient in the blue-green end of the spectrum as in the red end. PMT's optimized for the blue-green end of the spectrum also have lower dark current, i.e., unwanted signal when no scattered light is being detected, which results in less noise. Because the amount of scattered light compared to the incident light intensity is very, very small, noise considerations are extremely important in scattered light detector design and high intensity incident light is important to keep the intensity of scattered light at measurable levels. Further, the amount of light scattered is proportional to $1/\lambda^4$. Thus blue light which has a shorter wavelength $\lambda$ scatters much more than red light. A typical Helium-neon laser output is 633 nm. A typical line from an arc lamp which can be used is 467 nm. $633^4$ divided by $467^4$ is 3.4 which means the bluer light of he arc source scatters 3.4 times better than He-Ne laser light. Thus, it is highly desirable to use a PMT optimized for the blue-green. Lasers which output light in the blue-green end of the spectrum and have high output power are very expensive and very large. This makes the instrument bulky, heavy and expensive.

Further, lasers have ripple noise, i.e., noise modulated onto their output light intensity which is in the range from 0 to 30 Hz. Variations in the intensity of the incident light caused by the source translate into noise in the form of variations in the intensity of the scattered light not caused by the concentration or molecular weight of the scatterers. High performance liquid chromatography runs generally last from 30 to 90 minutes, and the output signals from the detectors are generally sample once per second. Thus, the sampling frequency is close to or within the frequency band of the ripple noise which tends to create further noise in the data.

Figure 3:
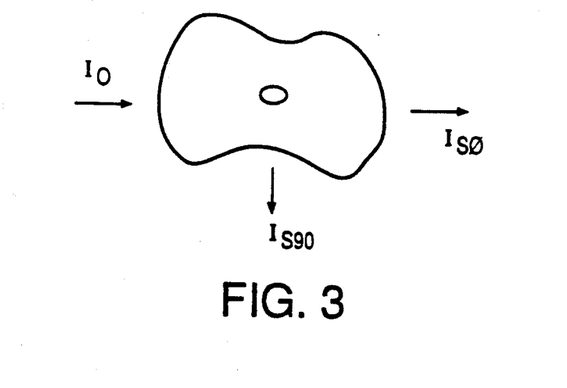
FIG. 3 is a scattered light intensity versus angle diagram for small particles.
Figure 4:
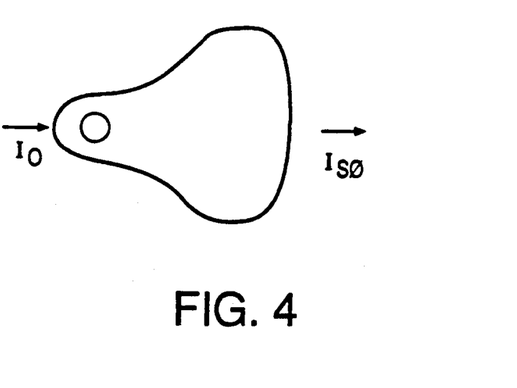
FIG. 4 is a scattered light intensity versus angle diagram for large particles.

Finally, another noise problem exists because of the inevitable presence of the very large particles in the output stream of the liquid chromatography column. These large particles possibly fines of column packing, and thus are not particles of interest, but, because of their large size, they cause a great deal of scattered light anyway. FIG. 3 illustrates the typical light scattering pattern of a small particle as a function of angle, and FIG. 4 illustrates the typical light scattering pattern of these large particles. In FIG. 3, the incident light vector $I_0$ enters from the left and the scattered light vectors for light scattered at low angles and at approximately 90 degrees are represented by vectors $I_{s0}$ and $I_{s90}$, respectively. The intensity of light scattered at 90 degrees from small particles is approximately one-half the intensity of light scattered at low angles. Unfortunately, as seen in FIG. 4, the intensity of scattered light from large particles has a very different shape. FIG. 4 illustrates that very little light is scattered at 90 degrees from large particles, and most of the scattered light is forward at small angle. This means that these large particles, despite their relative scarcity, will cause large noise spikes in low angle scattered light detectors.

Accordingly, a need has arisen for a new design for a classical light detector and system for determining molecular weight of biological proteins and other small particles that enter a scattering volume of a flow cell.

SUMMARY OF THE INVENTION

An apparatus according to one teaching of the invention comprises an arc light source, preferably, a mercury arc, a filter, a flow cell, an LC column, a UV detector, a high angle scattered light detector, an incident light detector and a computer to calculate molecular weight based upon signals from the UV detector and the scattered light detector. Light from the arc light source is filtered to leave one frequency, preferably a frequency with no analyte absorbance or fluorescence and in the band where the product of the intensity versus wavelength characteristics curve of he light source and the efficiency versus wavelength characteristic curve of the detector is at or near the maximum. This single wavelength light is optionally polarized to eliminate all but vertical polarization. An optical system then preferably focusses the filtered, polarized light to image the arc within the confines of the input window of the flow cell. The incident light detector preferably detects the intensity of the light incident on the flow cell input window.

The output stream from the LC column containing biological proteins from the sample is passed through the scattering volume of the flow cell associated with the scattered light detector. The intensity of light scattered at any angle between 35° and 145° can be used, preferably 90°, for ease of construction is then measured by the scattered light detector.

The UV detector has its own flow cell through which the output stream from the LC column passes. The UV detector detects the degree of absorbance of UV radiation by the biological particles (or other molecules) eluting from the LC column as they pass through the flow cell of the UV detector. This UV absorption data is typically done at a wavelength of 280 nm. But it may also be done at shorter wavelengths such as 200–214 nm, because not all proteins absorb at 280 nm, but substantially all proteins of interest absorb at 200–214 nm. Absorbance, at 280 nm is characteristic of protein concentration and can be used to calculate the weight concentration of the scatterers in the LC output stream. Any detector that provides a signal or data proportional to the weight concentration can be used for this purpose such as a refractive index detector. This concentration detection can be done upstream of the flow cell for the scatterometer light detector or downstream thereof but the data from the UV detector will need to be matched in time with the data from the scattered light detector as a result of the physical delay caused by travel time between the two detectors. This allows the weight concentration data derived from the UV detector data be matched with the scattered light intensity data thereby allowing the computer to correctly calculate the average molecular weight $\overline{M}_w$ of the scatterers as they elute from the LC column. This calculation is made using equation (3) below which is a simplified version derived from equation (1) above.

$$I_s/I_0 = B^* C^* M_w \quad (2)$$

where $I_s/I_0$ = the intensity of the high angle scattered light at some angle between 35° and 145° relative to the intensity $I_0$ of the light incident on the flow cell (this ratio cancels noise caused by variations in the output intensity of the light source), $\underline{C}$ = the weight concentration, $\overline{M}_w$ = the weight averaged molecular weight of the scatterers in the portion of the output stream for which the weight concentration C was calculated, and B = an optical constant which is different for each system and which is measured either empirically using several different types of particles of known weight averaged molecular weight of absolutely using a solution of known scattering ability such as Toluene.

An alternative apparatus according to the teachings of the invention uses a single flow cell with two output windows. A single light source is used. The focussing optics, and scattered light detectors can be structured as in the embodiment described above. The weight concentration data is determined using a UV detector, a monochromator and a second output window in the flow cell and two separate filters in front of the two detectors. The monochromator, i.e., a tunable filter that also passes harmonics, is tuned to filter light from the arc source to pass a wavelength suitable for measuring UV absorption, generally around 280 nm (or 200–214 nm depending upon the protein) and a second wavelength at about 560 nm is also passed, one being the fundamental and the other being the second order harmonic. The 280 nm wavelength is passed at a lower intensity. Not all proteins absorb at 280 nm so the monochromator may need to be tuned to pass 200–214 nm where virtually all proteins absorb. The wavelengths 400–428 nm also scatter well. Another advantage of using an arc as opposed to a laser is that the incident light frequencies can be more easily tuned. These wavelengths enter the flow cell and the majority of the incident energy passes straight through the flow cell without being scattered. The straight through energy exits from a window opposite the input window and is filtered by a filter which filters out all but the 280 nm light. This light is then detected by a UV PMT, and the resulting signal is digitized, subtracted from the intensity of the incident light and used to calculate the weight concentration.

A small fraction of the incident light is scattered at high angles between 35° and 145°. In the preferred embodiment the light scattered at about 90° is guided via a light path including a filter which leaves only the 560 nm light. This light is detected by a scattered light detector. The incident light intensity is also detected at the input side of the flow cell. This incident light intensity is used for ratioing with the scattered light intensity to cancel out noise arising from changes in intensity of the light entering the flow cell. It is also used to normalize the transmitted light intensity to cancel any noise therein created by variations in the output intensity of the light source. The normalized scattered light intensity and the weight concentration are then used to calculate the average molecular weight. This apparatus eliminates a noise source caused by the use of two flow cells and two light sources whose output intensity may be varying in other than a synchronized fashion.

A method according to one embodiment of the teachings of the invention comprises filtering intense incident light to leave only a first wavelength suitable for measuring weight concentration and a second wavelength in the band of highest sensitivity of a scattered light detector. Typically there is a function of generated light intensity at different wavelengths for the source and output signal magnitude versus wavelength for the detector. Preferably, the incident wavelength is chosen in a region of the spectrum where the product of these two functions is a maximum. A sample of biological proteins of other very small particles is then passed through a separation device and the stream of separated particles is passed through a transparent area, preferably a flow cell. The intensity of the light transmitted through the transparent area or flow cell without scattering at the wavelength suitable for measuring weight concentration is then detected using a known relationship and the weight concentration is calculated. Also, the intensity of light at the second wavelength at high angles in the range from 35°–145° (preferably near 90° for ease of construction) is measured. The intensity of the light which is incident on the flow cell is also measured at the input light side of the flow cell for noise cancellation purposes, i.e., to normalize the intensities of the scattered light and transmitted light. The scattered light intensity and the weight concentrations are then used to calculate the average molecular weight of the particles that caused the scattered light using a predetermined relationship such as equation (3) above.

Another method according to the teachings of the invention is: separate the small particles of interest (smaller than $\lambda/4$) by any known method such as liquid chromatography or capillary electrophoresis; pass a stream of the separated particles through a transparent zone, preferably a flow cell and measure any optical characteristic which can be used to calculate weight concentration of the particles and calculate the weight concentration; pass the stream through a second flow cell and shine intense light at one known wavelength $\lambda$ on the stream; measure the intensity of the light incident on the stream and the light scattered at any angle between 35° and 145°; and calculate in a computer the average molecular weight using equation (3) above and the weight concentration and the scattered light intensity normalized to the incident light intensity or simply output the scattered light and incident light intensities as separate signals or a ratio such that the calculation can be done manually. In an alternative embodiment of this method, a single flow cell and single light source filtered to leave two wavelengths could be used. One wavelength would be suitable for measuring UV absorption of light transmitted through the stream so as to calculate weight concentration. The other wavelength would be suitable for measuring scattered light such that the weight averaged molecular weight could be calculated using the relative scattered light intensity (normalized to the incident light intensity) and the calculated weight concentration. This method eliminates an extra source of noise which results if two noisy light sources are used where the variations in output light intensity of the two different sources are not tied together.

Another method and apparatus to practice the invention for large particles about which some things are known before hand is to make all the measurements described above. Then, the relationship between average molecular weight and the radius of gyration is looked up in a handbook of known properties. Many such tables exist. Of course one must know about the particles certain things and, in particular, the criteria upon which the tables are based such as their shape, size, the solvent etc. The tables usually give $\overline{M}_w$ in terms of $dRg^x$ where x is some power and a density factor d is given by the table. The equation relating $R_g$ to $\overline{M}_w$ is then rewritten to express $\overline{M}_w$ in terms of $Rg^2$ and the result is substituted for $Rg^2$ in equation (15). This rewritten equation (15) is then substituted into equation (11) for $P(\theta)$ to give a quadratic equation defining a relationship between light scattering potential R and weight averaged molecular mass $\overline{M}_w$. This relationship (equation (11) as rewritten) is then solved for $\overline{M}_w$ using the measured value for normalized scattered light intensity $I_s/I_o$ and either ignoring the viral coefficient terms if possible or using measured values for these coefficients. This works for any sized particles for which a sufficient amount of information is known so as to select the right table and the right criteria a priori. Of course, if the viral coefficient terms of equation (11) are nonnegligible for the large particles, these must be measured and used in equation (11) when solving for $\overline{M}_w$.

DETAILED DESCRIPTION OF THE PREFERRED EMBODIMENT

Figure 5:
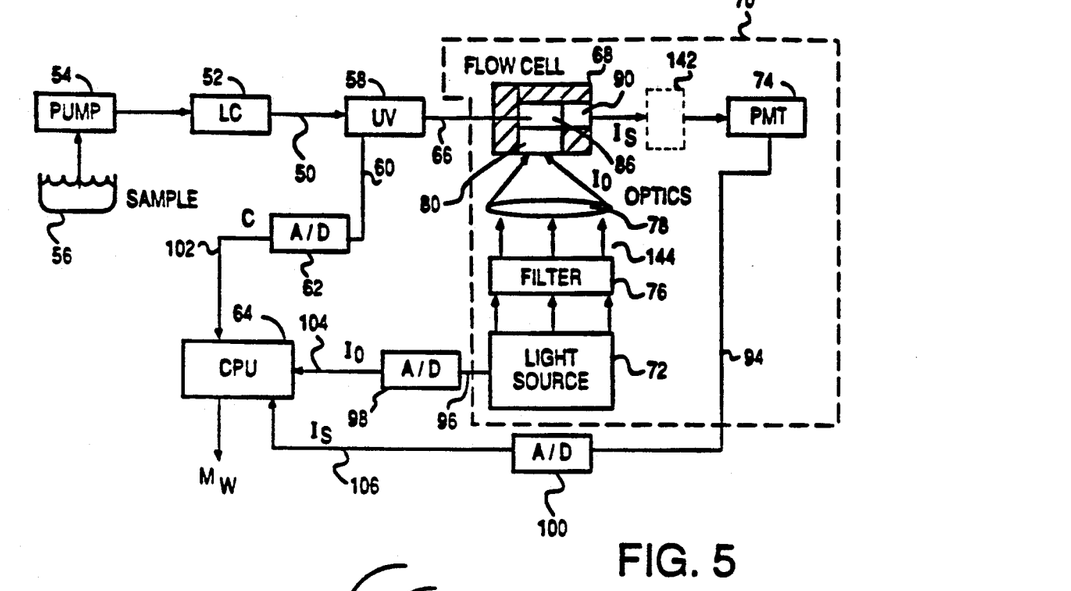
FIG. 5 is a block diagram of one embodiment according to the teachings of the invention of a high angle scattered light detector capable of calculating average molecular weight.

Referring to FIG. 5, there is shown a block diagram of one embodiment according to the teachings of the invention. FIG. 5 illustrates only one possible species of a class of systems that can calculate the average molecular weight of biological proteins and other small particles which have a size much smaller than the wavelength of light to be scattered. A typical application is to analyze LC chromatograms or to control collection equipment (not shown) coupled to the stream output 50 of an LC separation column 52 such that particles in the stream of specified molecular weights are collected in different containers. The system has other applications as well besides in the liquid chromatography field. For example, the system of FIG. 5 and all other embodiments disclosed herein can determine the molecular weight of small particles in a static solution.

In FIG. 5, a pump 54 pumps sample containing a mixture of biological proteins or other similarly sized particles from a container or other source 56. The sample is pumped through the liquid chromatography column 52 and is separated by some criteria such as size. The various sized particles then elute at different times from the LC column embodied in a stream of solvent on output 50.

To calculate the average molecular weight of the proteins eluting at any particular time, it is necessary to know the weight concentration of these proteins in the solvent stream. This can be verified by a study of equation (1) above. To do this, a conventional ultraviolet absorption detector 58 is coupled to the output stream 58 although any other type detector which is capable of generating an output signal from which weight concentration can be derived will also suffice. Such other types of detectors include refractive index detectors.

Typically the UV detector 58 will include a flow cell through which the solution containing the proteins flow, an ultraviolet source, an incident UV intensity detector, a transmitted UV intensity detector and other filtering and/or baffling and optical structures to increase the signal to noise ratio. A flow cell is basically a channel through a glass or quartz block with an input window to allow radiation to shine on fluid flowing through the channel and at least one output window for allowing scattered or transmitted light to leave. The manner in which the weight concentration is determined is not critical to the invention, and any method or apparatus which can make this determination will suffice for purposes of practicing the invention.

The UV detector 58 outputs an analog signal on line 60 which is either equal to or proportional to the weight concentration. This signal is converted to a digital signal by an analog-to-digital converter 62 and is input to a central processing unit (CPU) 64.

The solution stream leaving the UV detector 58 then traverses a channel 66 and enters a flow cell 68 (shown by a top or plan view) associated with a classical high angle scattered light detector 70 similar to the structure of light detectors that are often found in fluorometers. The detector 70 is comprised of a flow cell 68 which is optically coupled to a light source 72 to receive incident light $I_o$ and to a scattered light detector 74 located so as to sense the intensity of light $I_s$ scattered at right angles to the incident light $I_o$. Preferably, the light source 72 is a mercury arc lamp such as the 100 watt Osram HBO 100 W/2 arc lamp. The light source emits many different wavelengths, but from a study of equations (1) and (2), it will be noted that a single known wavelength must be used to mathematically derive the molecular weight. Either of two wavelengths are preferred. They are 436.1 nm which is a green color or 546.1 nm which is a green yellow. These two wavelengths lie in the band of greatest sensitivity and lowest dark current noise for the scattered light detector 74. Preferably, this scattered light detector is a photomultiplier tube (PMT) optimized for the blue-green region.

In alternative embodiments, the light source could be a xenon arc or tungsten lamp or a laser, but mercury arc lamp is preferred because of its higher intensity. Higher intensity incident light $I_o$ shining on the proteins in the solution flowing through the flow cell yields greater intensity for the high angle scattered light (as does greater weight concentration C of the proteins in the solution). Since only a tiny fraction of the incident light is scattered, higher intensity for the incident light yields a better signal to noise ratio because of the higher intensity for the scattered light. The output of a mercury arc lamp of the type suggested is approximately 20 milliwatts whereas the power output of a typical helium neon (HeNe) laser is 2-3 milliwatts with a wavelength of 633 nm. The HeNe laser wavelength does not provide maximum sensitivity if a PMT is used for detector 74. However, avalanche photodiodes could be substituted for the PMT since they are more sensitive to the red wavelengths. Xenon arc lamps typically yield only about ⅛th the intensity of output light of a mercury arc lamp so use of a xenon arc lamp is not optimal.

Further, both arc sources are preferred over a laser light source because lasers have ripple noise superimposed upon their output light intensity which is in the frequency range 0–30 Hz. Thus the same frequency band in which liquid chromatography sampling rates generally fall and can cause unwanted noise.

The light source 72 generates light which must be filtered to eliminate light at all but one frequency. Filter 76 performs this function. In alternative embodiments a tunable filter such as a monochromator can be used, but these devices are more expensive and bulky than are necessary. An inexpensive single wavelength filter in the blue-green region is preferred if a blue-green optimized PMT is used for detector 74.

Figure 6:
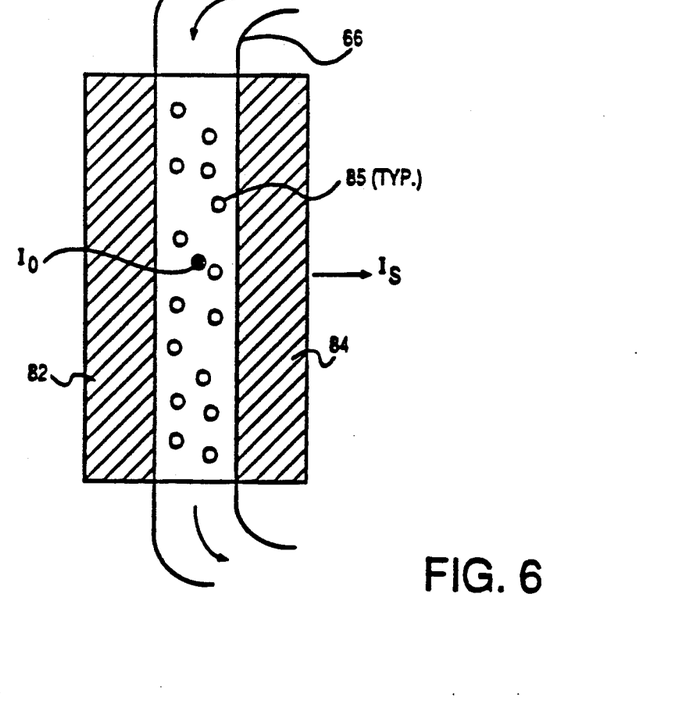
FIG. 6 is an elevation view of a flow cell input window.

The filtered light is then focussed by optics 78 onto an input window 80 of the flow cell. Generally, the input window is of a rectangular shape and is surrounded by black glass or glass coated with a black coating. FIG. 6 is an elevation view of the input window of a flow cell. The input window 80 is surrounded on at least two sides with black or black coated glass 82 and 84. The optics 78 focus the image of the arc within the confines of the input window 80 to minimize scattered light.

The proteins or particles of interest 85 enter the flow cell from channel 66 and pass down through a scattering volume 86 which is exposed to incident light $I_o$ through input window 80.

Generally, great care must be taken to prevent any of the incident light from the light source from getting to the PMT 74 and being detected as scattered light from the proteins 85 in the scattering volume. This means that baffling and a carefully controlled optical path (not shown) or fiber optic light guides (all of conventional fluorometer type design) are used to minimize scatter. The black glass portions of the flow cell also help prevent stray light scattered at air-glass or glass-solvent interfaces from being internally reflected and exiting the flow cell in the general direction of the PMT 74 where it would be detected as background noise. The black glass portions of the flow cell are shown as crossbatched areas in FIGS. 5 and 6. To aid in preventing scatter, fiber optic light guides may be used in the optical paths from the light source 72 to the input window 80 and from a scattered light output window 90 to the PMT 74. Index matching cement is used in these embodiments to fasten the fiber optic light guides to the input and output windows to minimize scattered and/or refracted light at the interfaces where the index of refraction changes from the index of the fiber optic care to the index of the glass of the flow cell.

The scatterer proteins 85 scatter the incident light $I_o$ based upon their molecular weight (classical Rayleigh scattering). Some of this light is scattered at high angles and exits the output window 90 as the scattered light $I_s$. This light is detected by PMT 74 and an output signal proportional to its intensity is output on line 94. In addition, the scattered light detector 70 also outputs a signal which is proportional to the intensity of the incident light $I_o$ on line 96. In some embodiments, a single output signal equal to $I_s I_o$ is output. Preferably, the intensity $I_o$ of the incident light is detected by a detector (not shown) optically coupled so as to "see" light as it enters the input window. This may be done using a beam splitter (not shown) in the optical path from the filter to the input window to reflect some of the incident light to an $I_o$ detector (also not shown) or in any of a number of different ways. It is preferred to sense the intensity $I_o$ after filtering the light from the source such that $I_o$ is a true indication of only the incident light reaching the scatterers and not the total intensity of all wavelengths output by the light source. In alternative embodiments the PMT 74 is cooled or is a photon-counting type device.

The scattered light intensity $I_s$ signal on line 94 and the incident light intensity $I_o$ signal on line 96 are converted to digital signals by analog-to-digital converters 98 and 100.

The CPU 64 then computes the molecular weight of the scatterers by correlating the weight concentration data on line 102 with the $I_o$ and $I_s$ data on lines 104 and 106. This correlation or matching of data takes into account the time delay for the scatterers to travel from the flow cell in UV detector 58 to the flow cell 68. Once the data is properly correlated, the average molecular weight of the scatterers is calculated using equation (3) above.

Equation (3) is a simplification of equation (1) above and is derived as follows.

The relationship between the intensity $I_o$ of light used to illuminate a sample, the pathlength 1 of the scattering volume and the amount of light $I_t$ which is transmitted through the sample is $$I_t = I_o e^{-(\tau C + \epsilon)l} \quad (3)$$

where
$\epsilon$ = the extinction coefficient
$C$ = the concentration of the sample
$\tau$ = the turbidity of the sample which is a measurement of the solution's ability to scatter light, and
$l$ = the path length of the scattering volume In the absence of absorption, $\epsilon = 0$ and equation (3) becomes $$I_t = I_o e^{-\tau l} \quad (4)$$

Conservation of energy requires that $$I_t = I_o - I_s \quad (5)$$

meaning that the intensity of the transmitted light which passes through the solution is equal to the intensity of the incident light minus the intensity of the scattered light.

Since the intensity $I_s$ of the scattered light is quite small relative to the incident light intensity, (5) and (6) can be combined, the exponential can be expanded in a Taylor series and only the first two terms need be kept. This yields $$I_s/I_o = \tau l \quad (6)$$

It is possible to measure the turbidity of the sample by measuring $I_t$ and $I_o$ and using equation (6). This is called a "turbidimetric" measurement. If the scattered light intensity is measured and equation (7) is used, this is called a "nephelometric" measurement. In turbidimetric measurement, one needs to measure a small difference between two large numbers ($I_t$ and $I_o$). In nephelometric measurements, $I_o$ is large while $I_s$ is a small quantity but one which is measured against a small background. Nephelometric measurements are therefore usually much more sensitive and accurate are the more useful of the two techniques. Both techniques are variants on classical light scattering methodology.

Typically, the scattered light intensity is not measured at all angles. Rather, only the amount of light scattered into some solid angle at an angle $\theta$ relative to the incident light $I_o$ is measured. $I_s$ and $i\theta$ are related by $$I_s = \sum_{\text{all angles}} i_s^\theta \quad (7)$$

Rewriting equation (7) using equation (8) yields $$\frac{i_s^\theta}{I_o} = \tau^\theta l \quad (8)$$

where
$\tau^\theta$ = the fraction of the turbidity responsible to light scattered at angle $\theta$.

In analogy to Beer's law for absorption, we have:

$$\frac{i_s^\theta}{I_o} = \tau_{sp}^\theta \, c \, l \quad (9)$$

where
$C$ = the weight concentration
$\tau_{sp}^\theta$ = the specific turbidity or the "specific Raleigh constant" as it is sometimes called.

The specific turbidity is an interaction cross-section (a probability that certain interaction will occur). For purposes of practicing this invention, scattered light intensity is measured at 90° although any other angle could also be used. The specific turbidity at this angle is denoted $\tau_{sp}$.

The specific turbidity can be related to the molecular properties of the particles interacting with the incident radiation.

$$\frac{K}{\tau_{sp}^\theta} = \frac{1}{M_w P(\theta)} + 2A_2 C + 3A_3 C^2 \quad (10)$$

where the terms are as previously defined for equation (1) above specific turbidity $\tau_{sp}^\theta$ is proportional to R/C or Raleigh scattering divided by the weight concentration.

If the specific turbidity $\tau_{sp}^\theta$ has been measured, equation (11) can be used to derive $M_w$, the weight-averaged molecular mass of the scatterers. The weight-averaged molecular weight of the scatterers. $M_w$ is defined as $$M_w = \frac{\sum_i c_i M_i}{\sum c_i} \quad (11)$$

where
$C_i$ = the weight concentration of the ith component of the solution, and
$M_i$ = the mass of the $i^{the}$ component of the solution Since the weight concentration is equal to the number concentration $n_i$, times the molecular mass $$M_w = \frac{\sum_i n_i M_i^2}{\sum_i n_i M_i} \quad (12)$$

Equations (12) and (13) show that M is heavily weighted toward the higher mass components of the solution, so $\tau_{sp}^\theta$ will also be heavily influenced by the more massive particles.

The optical constant K in equation (12) is $$K = \frac{4\pi^2(ndn/dc)^2}{\lambda_o^4 N_a} \tag{13}$$

where
n = the refractive index of the solution in which the scatterers are entrained
dn/dc = the change in refractive index of the solution as the concentration of the solution is altered,
$N_a$ = Avagadro's number, and
$\lambda$ = the wavelength of the incident light.

The dependence of K on the fourth power of $\lambda$ is valid only for particles whose dimensions are less than $\lambda/4$. For larger particles, the wavelength dependence is a complicated function of the size of the scatterers, but, in general, the larger the scatterer, the smaller the power dependence.

$P(\theta)$ is a size parameter which had prior art workers confounded. For small particles whose size is less than $\lambda/4$, $$P(\theta)^{-1} = 1 + \frac{16\pi^2 n^2 R_g^2 \sin^2\theta/2}{3\lambda_o^2} \tag{14}$$

where
$R_g$ = the radius of gyration of the scatterers, which is generally size dependent.

If $\tau^\theta_{sp}$ at several scattering angles, equation (15) can be used to determine $R_g$. For roughly globular particles:

$$R_g^2 = \frac{2}{5} R^2 \tag{15}$$

where
R = the radius of the sphere which can usually be approximated by the radius of hydration or Stokes radius of the scatterers.

The smaller the scattering angle $\theta$, the weaker the dependence of $P(\theta)$ on the size of the scatterer. Thus, low angle photometers such as LALL detectors do not show a strong dependence of turbidity on size since sin $\theta/2$ is approximately 0 at small $\theta$.

However, importantly, regardless of scattering angle $\theta$, $P(\theta)$ is approximately equal to 1 for scatterers with a radius less than $\lambda/20$. A protein whose radius is $\lambda/20$ for visible light (488 nm) has a mass of approximately $20 \times 10^6$ Dalton (1 Dalton is equal to 1 gram per mole of a substance). The largest protein typically of any biological interest, $I_gM$, has a molecular weight of $1 \times 10^6$ daltons. Larger proteins than this have no clinical, therapeutic or diagnostic uses so far. Thus, for all biological proteins of interest, $P(\theta)$ is approximately 1 at any scattering angle because the radius of gyration $R_g$ is very small based upon the small sizes of these proteins.

One may also use approximations for $P(\theta)^{-1}$ based upon known relationships between $M_w$ and $R_g$ for certain shapes of particles if one desires to use high angle scatter light detection on large particles. For example, it is known that for random coil polymers $$M_w \text{ is proportional to } d R_g^2 \tag{16}$$

where
d = a density factor that can be looked up in a handbook having tables for random coil polymers.

Thus, if it is known that random coil polymers are the only types of polymers in the flow cell, one can substitute $M_w/d$ for $R_g^2$ in equation (15) and substitute the rewritten equation (15) for $P(\theta)^{-1}$ in equation (11) yielding a quadratic equation relating $M_w$ to Rayleigh scattering R or turbidity $\tau^\theta_{sp}$.

For globular shaped proteins, $$\overline{M}_w \text{ is proportional to } d R_g^3 \tag{17}$$

In this case $$P(\theta)^{-1} = 1 + \frac{16\pi^2 n^2 \left(\frac{\overline{M}_w}{d}\right)^{2/3} \sin^2\theta/2}{3\lambda_2} \tag{18}$$

which can be substituted in equation (11) and solved analytically.

Furthermore, in some cases it may be desirable to maintain the terms in equation (11) involving the viral coefficients. These can be measured by carefully measuring $I_s$ versus concentration C and looking for the small deviations caused by $A_2C$ etc. Most of the time, this is not necessary.

Equation (11) above is a power series expansion in weight concentration with coefficients which reflect the strength of the intra-particle interactions. The first order coefficient, $A_2$, is known as the second viral coefficient and is proportional to the volume of the scatterer within which another particle cannot enter, namely the excluded volume. For strong solvents, $A_2$ is small but positive. As the solvent strength decreases, $A_2$ decreases to zero and becomes negative as the particles begin to interact, i.e. aggregate. For most proteins in "physiological" buffers (e.g. greater than 10 mm salt and pH of approximately 7), $A_2$ is approximately 0 or slightly negative. Further, owing to the relatively low solubility of most proteins, concentrations at which higher order terms become significant are inaccessible during chromatography. For such particles or proteins as Proleukin IL-2 (a mixture of protein and a detergent), the first order term of equation (11) needs to be included. However, for most biological proteins, equation (11) can be simplified to $$\tau^\theta_{sp} = KM_w \tag{19}$$

By substituting equation (10) for $\tau^\theta_{sp}$, equation (19) can be rewritten in the form of equation (2) above which is used by the CPU 64 to calculate the weight averaged molecular weight $\overline{M}_w$ of the scatterers.

The value of B varies from one embodiment of the invention to another but can be easily measured for a specific system using toluene to calibrate the system since toluene has a known turbidity.

Any circuit or device which can make the calculation of equation (3) will suffice for purposes of practicing the invention. In fact, in the broader aspects according to the teachings of the invention, the CPU 64 or other calculating device can be eliminated since the molecular weight $M_w$ may be easily calculated by hand from the scattered light intensity and the concentration.

Figure 7:
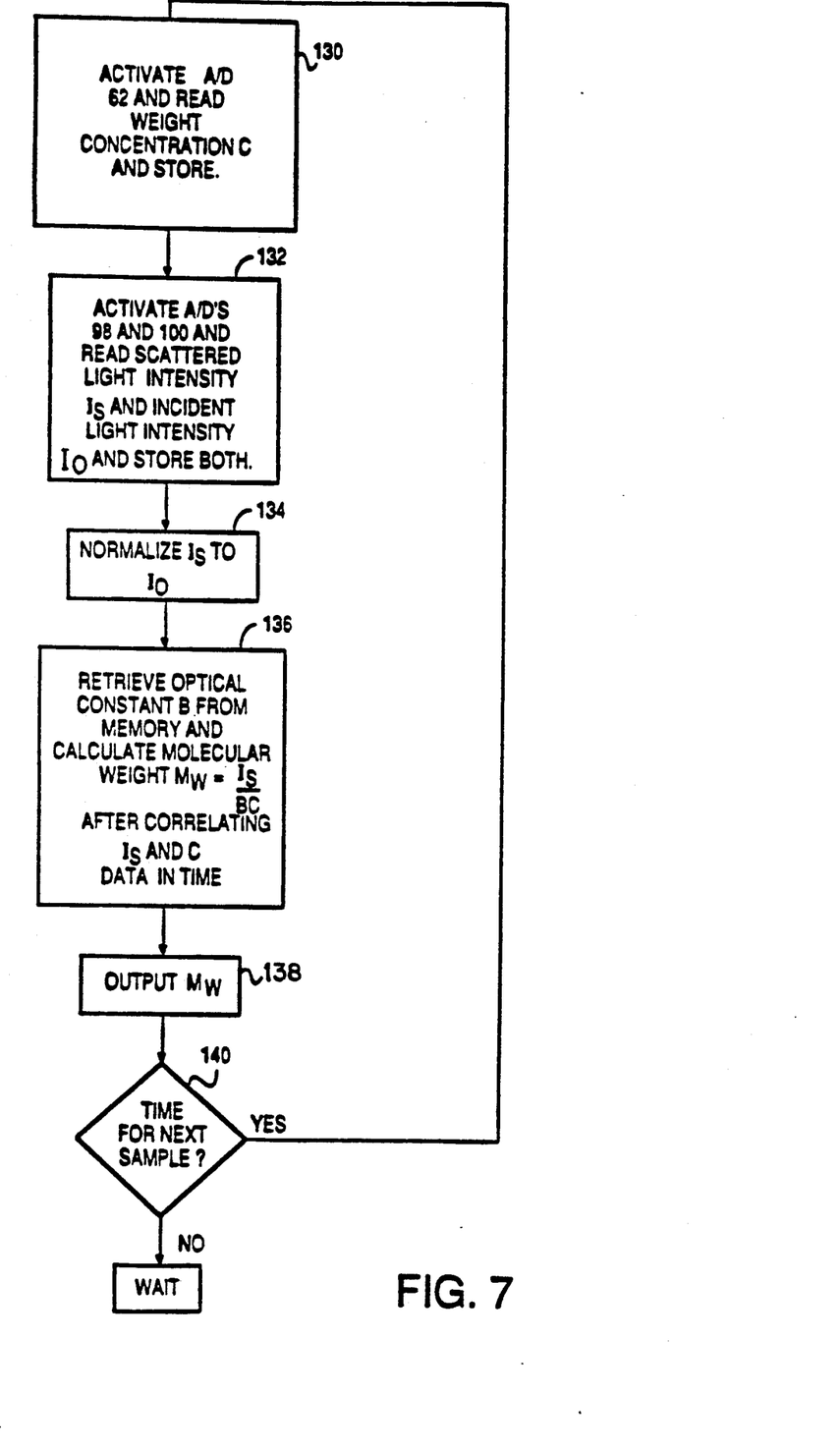
FIG. 7 is a flow chart of a typical program for controlling the computer in FIG. 5 to calculate the average molecular weight of the scatterers.

Referring to FIG. 7, there is shown a flow chart for a typical program for controlling the CPU 64 of FIG. 5 to calculate the average molecular weight $M_w$ of the scatterers in flow cell 68. A typical program for controlling the CPU 64 will sample the scattered light intensity and concentration C signals every second, compute the average molecular weight for the particles yielding the data from the most recent sample or a moving average of sample and output the result. Typically, the program to calculate the molecular weight will be a subroutine which is called every second from a main control loop upon timeout of an internal timer. However, the program may also be structured as a main loop which runs during every sample period.

The sample period depends upon the desired resolution desired to resolve chromatogram data, i.e., how many peaks are expected over a one minute interval and how many samples are desired per peak. It also depends upon the amount of memory and/or hard disk storage capacity available to the CPU 64 to store the data.

The first step of the process is symbolized by block 130. In this step, the CPU activates the A/D converter 62 to cause it to convert the analog signal on line 60 to digital data in line 102 representing the weight concentration C. This data is then stored.

Next, in step 132, the A/D's 98 and 100 are activated to convert the analog incident light $I_o$ and scattered light $I_s$ signals to digital data. This data is then stored.

Step 134 represents the process of normalizing the intensity of the scattered light $I_s$ to the intensity of the incident light $I_o$. This is essentially the process of dividing $I_s$ by $I_o$ such that any variation in the intensity of $I_o$ caused by noise which is translated to noise in the scattered light $I_s$ is canceled.

Step 136 represents the process of calculating the average molecular weight of the scatterers using equation (3) by dividing Is by the product of B and C.

In step 138, the result calculated in step 136 is output and can be used by displaying it or using it to control a sorting decision apparatus etc.

Decision step 140 and its two branches is symbolic of any process which controls the rate of sampling.

Figure 8:
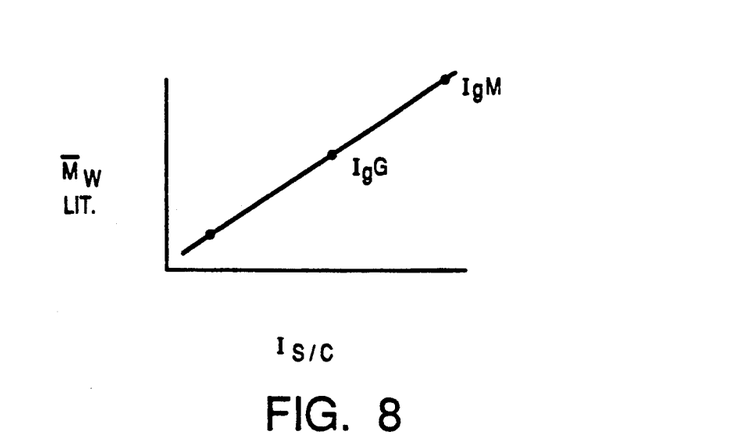
FIG. 8 is a graph of typical experimental results which illustrates how the optical constant B in equation (3) is experimentally determined for a particular high angle scattered light detector.

Referring to FIG. 8, there is shown a graph of scattered light intensity versus known molecular weight which is useful for experimentally determining the value of B for a particular optical system. To determine B, biological proteins or other small particles of known average molecular weight are passed through the flow cell in a known concentration. The scattered light intensity is then measured for each protein and plotted as $I_s/c$ at the level of the known average molecular weight. This has been done in FIG. 8 for two proteins of known average molecular weight $I_gG$ and $I_gM$. The resulting linear function inherently defines the value of B for that particular optical system.

The flow cell in FIG. 6 typically has a volume of 10 microliters, a path length of 10 mm and can be made of less expensive glass such as BK7. The expensive quartz flow cells commonly used in fluorometers need not be used because in these fluorometric devices quartz must be used to let in the short wavelength (200-280 nm) light needed to excite fluorescence. Typically, BK7 type glass cuts off radiation having a wavelength shorter than about 320 nm so this type glass cannot be used in a fluorometric light detector.

Overcoating the input window and output window faces of the flow cell with index matching $M_gF_2$ or multi-layer dielectric anti-reflection coatings would increase the signal and reduce background or stray light considerably. This creates a better match in index of refraction at the air-glass interface which reduces refractive bending which can cause spurious scattered light.

For the most demanding applications, the flow cell 68 is of the known "squeeze" design with the inner surfaces anti-reflection coated for the glass/water or glass-/solvent interface. Such flow cells are manufactured using two flat plates of glass each of which has one surface coated by chemical vapor deposition with a suitable anti-reflection coating. The two plates are then "squeezed" together with a sealing spacer therebetween to form the cell in a known process. The spacer has an input hole and an output hole formed therein for allowing flow through the cell. Since most solvents commonly used for biopolymers for HPLC, e.g., water, acetonitrile, methanol) have approximately the same index of refraction, this coating of the inside surfaces of the cell with an index matching material greatly reduces stray light scattered at the interfaces.

Larger arc light sources 72 may also be used if they are brought to a line focus within the confines of the input window. Not doing this will increase stray light which is largely responsible for background noise which is one of the problems which decreases such a detector's sensitivity.

In the preferred embodiment, the filter 72 (and the filter 142, if used) are Hg line interference filters rather than monochromators since this makes the design cheaper and smaller. In addition, the filter 76 can be used with a vertical polarizer, symbolized by dashed box 144. Only vertically polarized light can scatter. Horizontally light does not Rayleigh scatter so such light, if allowed to reach the flow cell, may become stray light and contribute to background noise.

Standard HPLC data systems such as those manufactured by P. E. Nelson can be modified to include the simple mathematical function of equation (3). Alternatively, they may be modified to include the more complicated equation (11) in some embodiments or variants thereof for larger particles about which some things are known a priori and to gather and store data and calculate the weight averaged molecular weight.

The extremely small volume for the flow cell is desirable because it retains the shape of peaks better. If a very narrow peak elutes from an LC column, and is transmitted to a flow cell via a microbare channel, the peak will be spread out by mixing with the contents of the flow cell if the scattering volume of the flow cell is large. Keeping the scattering volume small minimizes this spreading problem.

In some embodiments of the genus of machines symbolized by the structure of FIG. 5, a second filter is used in the scattered light path. These embodiments are symbolized by the dashed line filter 1423 in the optical path between the output window 90 and the PMT 74. This filter is tuned to the same wavelength as the filter 76 so that no stray light of a different wavelength can get into the PMT. This is different from a fluorometer where the filter 76 is set to the wavelength of the excitation light and the filter 142 is set to the different wavelength of the emitted fluorescent light. Some modern fluorometers do not allow both filters to be tuned to the same wavelength.

Further reduction in stray light could be achieved in any of the embodiments disclosed herein through.the use of integrated spatial filters.

Figure 9:
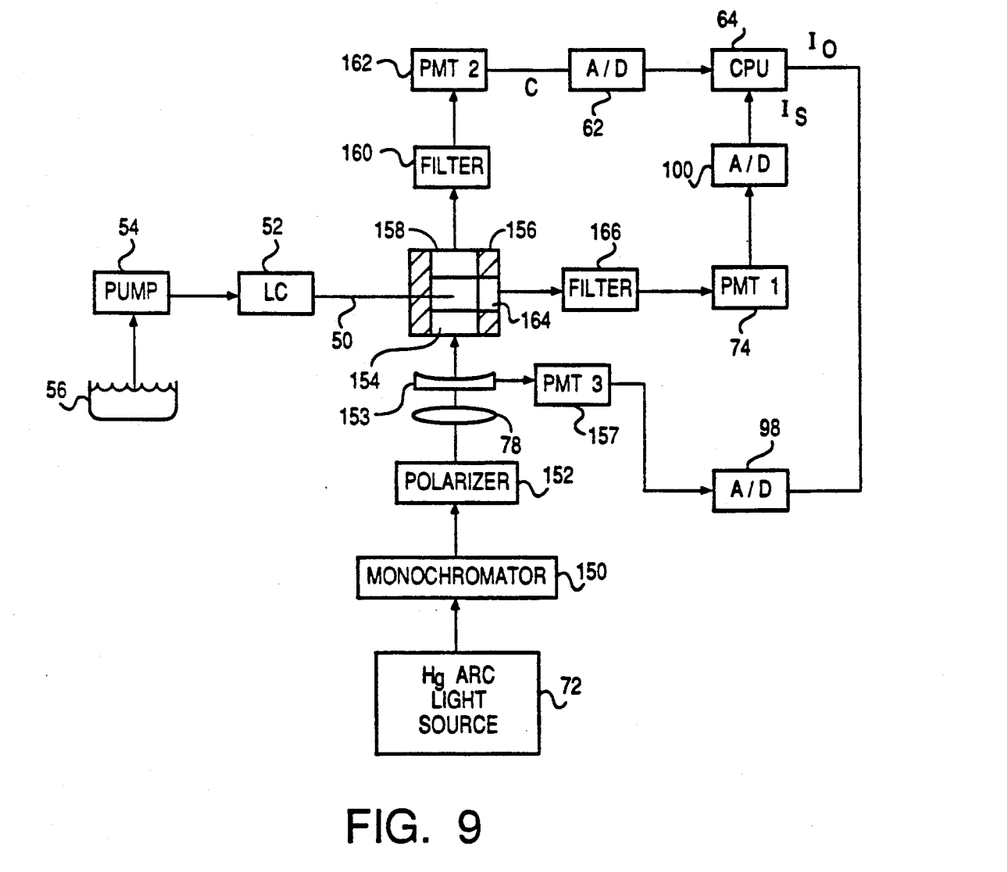
FIG. 9 is a block diagram of another embodiment of an apparatus according to the teachings of the invention showing how the weight concentration and scattered light detectors can share one flow cell.

Referring to FIG. 9, there is shown another embodiment for a high angle scattered light detector according to the teachings of the invention. The embodiment of FIG. 9 allows the weight concentration and scattered light intensity detectors to share the same flow cell. The pump 54, sample reservoir 56, LC column 52, light source 72, PMT 74, optics 78, CPU 64 and the A/D converters 98, 100 and 62 all operate in the same way as in the embodiment of FIG. 5 and are subject to the same functional equivalent substitutions.

The embodiment of FIG. 9 makes beneficial use of the principle of equation (4) and of the property of monochromators to pass harmonics. Typically, the weight concentration is determined using a UV absorption measurement at a short wavelength, i.e., around 280 nm. On the other band, the scattered light measurement is usually done at a wavelength which approximately twice as long as the UV absorption measurement wavelength. This allows the light scattering PMT to operate in its most sensitive range, i.e., around 560 nm. These two wavelengths can be obtained from the same source 72 by using a monochromator 150 to filter the incident light and tuning it to pass the 560 nm light. Because 280 nm is the second harmonic of 560 nm, light at this wavelength also passes through the monochromator. An optional polarizer 152 then filters out all but the vertically polarized light at 560 nm and 280 nm. This light is then focussed on the input window 154 of the flow cell 156 by the optics 78 through a beam splitter 154. The beam splitter directs a portion of the incident light to a PMT 157 which serves as a detector of the intensity $I_o$ of the light incident on the flow cell.

The flow cell 156 has generally the same structure and function as the flow cell 68 except that it has two output windows instead of one. The second output window 158 is positioned such that light not scattered by the particles in the scattering volume of the flow cell passes through the second output window 158. This nonscattered light will hereafter be referred to as the transmitted light $I_t$.

The transmitted light $I_t$ is filtered by a conventional interference filter or other inexpensive filter to filter out all light but the 280 nm light not absorbed by the scatterers. The intensity of this filtered light is sensed by PMT 162 and converted to digital data by A/D converter 62. The CPU 64 then calculates the weight concentration of the scatterers using equation (4). This is done under the control of software which is very similar in structure to that illustrated in FIG. 7 but which includes steps to gather and store data regarding the intensity $I_t$ of the transmitted light and the intensity $I_o$ of the incident light and then calculate the weight concentration C using equation (4) and stored constants for the extinction coefficient and the path length. The weight concentration so calculated is then stored for subsequent use in calculating the average molecular weight $M_w$ in the fashion shown in the process illustrated in FIG. 7.

The light scattered at high angles at or near 90° exits the output window 164 and is filtered by a filter 166. The filter 166 removes all wavelengths but the 560 nm wavelength. The filtered light is then detected by the PMT 74 and the resulting output signal is converted to digital data by the A/D converter 100.

The A/D converter 98 converts a portion of the incident light to the $I_o$ intensity data used by the CPU 64 to normalize the transmitted light intensity $I_t$ and the scattered light intensity $I_s$ data.

Generally, equation (4) may be simplified by a Taylor series expansion keeping only the first one or two terms to calculate the weight concentration as was the case for the scattered light exponential. In other embodiments, the exponent of equation (4) can be evaluated using $I_t$, $I_o$ and a natural logarithm look up table. The same is true for the exponential relating the average molecular weight to the scattered light intensity.

Because the extinction coefficient e in the exponent of equation (3) is so small for all biological proteins of interest, it can be ignored.

The advantage of the embodiment of FIG. 9 is that it eliminates one flow cell and the need for the CPU 64 to match up weight concentration data from one flow cell generated earlier or later in time than the light scattering data from a different flow cell. The two flow cells of the genus of embodiments illustrated in FIG. 5 cause generation of the C and $I_s$ data for the same particles at different times because of the time delay for particles passing through the flow cell of the UV detector 58 to reach the flow cell 68. This requires the computer 64 to match up the C data and $I_s$ data for the same particles even though these two sets of data were generated at different times. The correlation process is included in step 136 in FIG. 7.

The method and apparatus for finding the weight concentration using the transmitted light intensity $I_t$ described above works well if the extinction coefficient for the particles coming out of the LC column is known. The extinction coefficient $\epsilon$ is an intrinsic property of a molecule which indicates how much UV light the molecule will absorb on a weight basis or if it is known that the particles are all of one type but different configurations of that type. In the most general case, where the type and mass of the particles emerging from the LC column are not known, it is not possible to know the extinction coefficient. In such a case, the weight concentration data must be derived using a refractive index detector in a known fashion. Refractive index detectors can be used even in the case of gradient solvent makeup if the technology of a U.S. patent application entitled "Reference Flow Liquid Chromatography System With Stable Baseline",, Ser. No. 07/463,701, filed Jan. 11, 1990 (now U.S. Pat. No. 4,988,447) which was a divisional of Ser. No. 07/456,021 filed Dec. 22, 1989 (now U.S. Pat. No. 4,990,250) which was a continuation of Ser. No. 07/155,592, filed Feb. 12, 1988 (now abandoned) (and all published foreign patent applications corresponding to these cases) is used, all of which are hereby incorporated by reference.

In the case where all the same particles are eluting from an LC column but are eluting at different times because of different configurations and different sizes, the relative weight concentrations as among the various peaks can be determined using a UV detector or fluorometer without knowing the extinction coefficient. This is because the extinction coefficients are the same for all the differently sized particles, so the weight concentrations are related to the transmitted light intensity by the same function, equation (4) where $\epsilon$ is the same for every peak. This information can be used to determine the relative average molecular weight as among the various peaks which is analytically useful for interpreting chromatograms in this situation.

Methods according to the teachings of the invention include the operation of the embodiments of FIGS. 5, 9, 10, 11 and 12.

Figure 10:
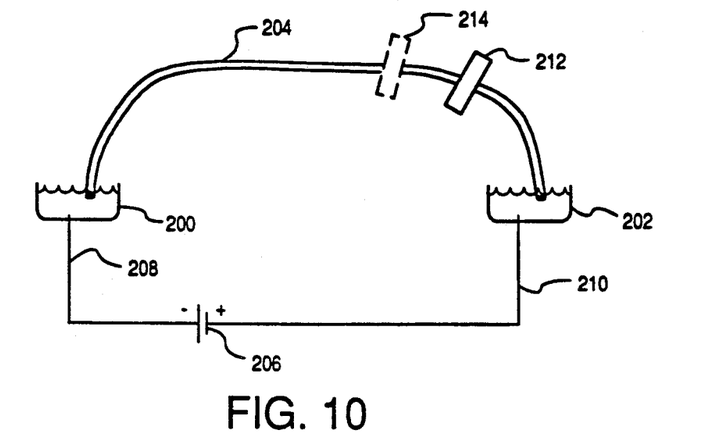
FIG. 10 is a diagram of an embodiment using capillary zone electrophoresis for separation of particles.

FIG. 10 is a diagram of another embodiment of the invention wherein the separation device is a known capillary electrophoresis structure. Capillary electrophoresis is a process wherein charged proteins or other molecules migrate along a capillary tube under the influence of an electric potential and travel at a rate dictated by their charge. Molecules or proteins having a higher charge travel faster than molecules having a lower charge. Particles of opposite charge travel in opposite directions. The different rates and directions of travel lead to separation along the length of the capillary tube and different arrival times at any particular point along the capillary tube.

The apparatus of FIG. 10 includes a first container 200 and a second container 202 in which the open ends of a fused silica capillary tube 204 are immersed. Typically the capillary tube bore is 25–100 $\mu$M inside diameter. Each of the containers 200 and 202 contains a low conductivity aqueous solvent. Sample is introduced into the capillary tube 204 in any known manner, typically by dipping one end of the capillary tube 204 into a container of the sample so as to introduce a few microliters of sample into the end of the capillary. The capillary is filled with the conductive solvent by any known means (not shown). A voltage source 206 having electrodes 208 and 210 in electrical contact with the solvent in containers 200 and 202, is used to apply a D.C. electric potential as between the solvent in container 200 and the solvent in container 202.

The electric field between containers 200 and 202 causes the charged analytes (sample proteins or other molecules) to immediately begin migrating along the capillary tube bore at different speeds. In the preferred embodiment, a flow cell 212 of the type previously described is coupled to the capillary such that the stream of migrating proteins or other molecules passes through the flow cell 212.

The flow cell 212 is optically coupled to an apparatus of the type shown in FIG. 9. This scattered light detector apparatus (not shown in FIG. 10) works the same way as described above to calculate the average molecular weight of the proteins or molecules as they migrate through the flow cell 212.

In another embodiment of this capillary electrophoresis separation device, a second flow cell 214 (shown in phantom) is coupled to the capillary 204 such that the proteins also pass through this flow cell. The flow cell 214 is part of the standard UV detector 58 in FIG. 5, and the flow cell 212 is optically coupled to a scattered light detector apparatus as shown in FIG. 5 (not shown in FIG. 10). This light scattering detector apparatus functions as described above. The normalized scattered light intensity developed by the scattered light apparatus coupled to flow cell 212 and the weight concentration data developed by the UV detector associated with flow cell 214 are used to calculate the average molecular weight as described above.

The average molecular weight of the eluting molecules, coupled with their arrival times which is indicative of their charge, can be used for analysis or identification of the particles. This type of separation technique is well suited to this type of scattered detection because of the small volumes, high analyte concentration leading to higher scattered light intensities, and the ease of on-column detection (real time) in both the absorbance and high angle scattered light configurations.

In some embodiments where a transparent capillary tube is used, the flow cells may be dispensed with, and the incident light shined directly on the capillary tube. Although this leads to more background scattered light from the tube itself, it can still work.

Figure 11:
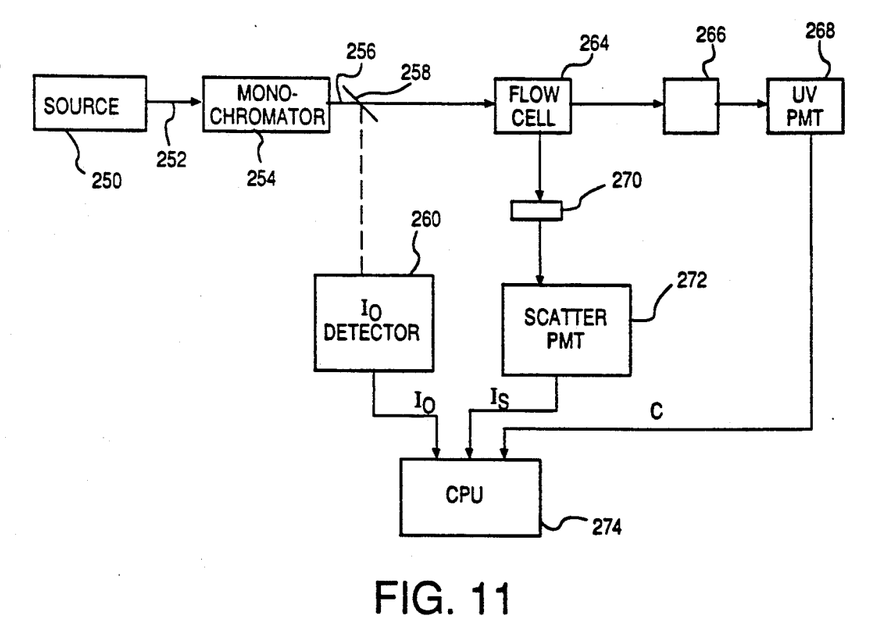
FIG. 11 is a diagram of an embodiment using a single light source, a single flow cell and a single monochromator.

Referring to FIG. 11, there is shown another embodiment of a "2-for-1" instrument using a single light source and a single flow cell. In this embodiment, a light source 250 having a broad band output spectrum that includes at least 200–300 nm and 400–600 nm wavelengths is used. The output light 252 is filtered by a monochromator 254 to leave wavelengths suitable for UV absorption and Rayleigh scattering measurements, preferably 280 nm and 560 nm but possibly some wavelength between 200–214 nm and 400–428 nm at 256. A partially silvered mirror reflects part of the incident light to a detector 260 for the incident light. This detector outputs an $I_o$ signal to CPU 262. A flow cell 264 passes most of both the 280 and 560 nm light to a filter 266. This filter blocks the 560 nm light, and a PMT detects the intensity of the 580 nm light. Light scattered at some high angle is filtered by a filter 270 to leave only 560 nm light which is detected by PMT 272. PMT 272 outputs a signal $I_s$ representing the scattered light intensity and PMT 268 outputs a signal C representing the weight concentration. The PCU 274 processes these three signals $I_o$, $I_s$ and C to calculate the weight averaged molecular mass as described above.

Figure 12:
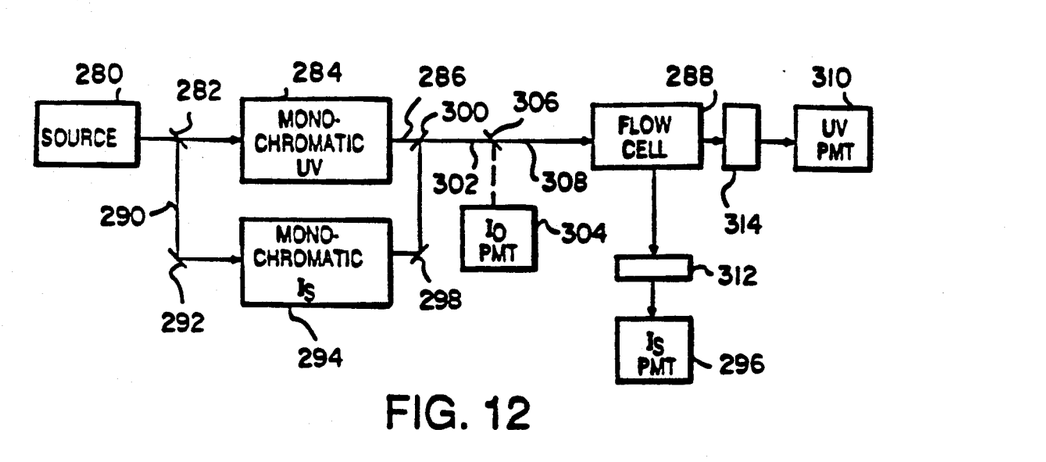
FIG. 12 is a diagram of an embodiment using a single light source and flow cell but using two monochromators.

Referring to FIG. 12 there is shown a more complicated "2-for-1" embodiment. In this embodiment, a single broadband source 280 generates light which is split by a beam splitter 282 into two beams. The first beam is filtered by a first monochromator to leave only a wavelength in the output beam 286 which is suitable for UV absorption measurements by the scatterers in a flow cell 288. A second beam 290 is reflected by a mirror 292 to a second monochromator 294. The second monochromator 294 filters out all wavelengths but a wavelength optimized for scattering. Typically this wavelength will be somewhere in the blue-green spectrum at a point at or near where the product of the characteristic curves for the source 280 and the scattered light detector 296 is at a maximum. This scattering wavelength need not be a harmonic of the wavelength in beam 286. The characteristic curves referred to above are the characteristic relating output light intensity of the source 280 at various wavelengths and the efficiency of the scattered light detector 296

The selected wavelength for scattering is reflected by mirror 298 and is recombined by partially silvered mirror 300 with beam 286.

The combined beam 302 has a portion thereof reflected away to an $I_o$ incident light detector 304 by a partially silvered mirror 306. The beam 308 of incident light is then applied to the flow cell 288. Scattered light and transmitted light are then detected and weight averaged molecular weight can be manually or electronically calculated from the outputs of detectors 304, 296 and 310. Filters 312 and 314 insure that only the proper wavelengths reach the detectors 296 and 310, respectively.

The advantage of the embodiment of FIG. 12 is that only a single light source is used so noise from two independent sources having unsynchronized random changes in their output intensity is eliminated. Further, the use of two monochromators allows the UV and scattering wavelengths to be separately tuned to optimize the UV absorption function for determination of weight concentration and the scattering function for determination of $M_w$.

Figure 13:
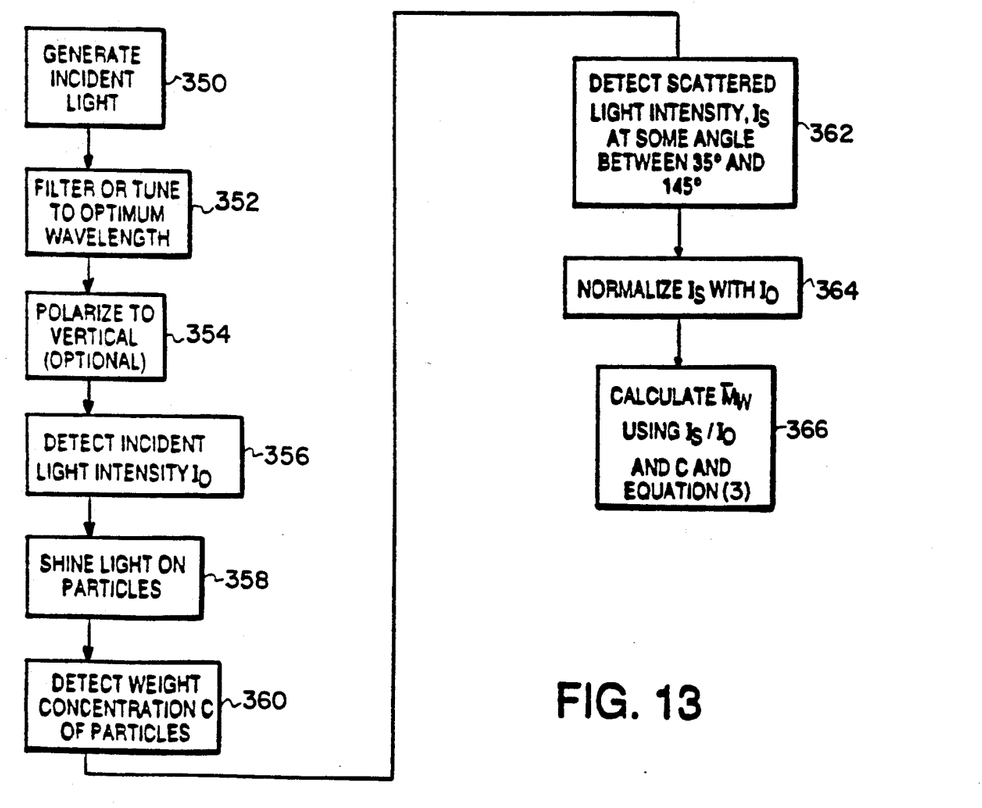
FIG. 13 is a diagram of a process for determining the weight average molecular weight using two flow cells and two light sources.

FIG. 13 is a flow chart of a method according to the teachings of the invention for multiple flow cell embodiments. Step 350 is generation of the incident 5 light, and step 352 represents the process of filtering or tuning this light to a wavelength which is optimum for scattering as previously described (where the product of the source and detector characteristic curves is a maximum). This step 352 can be done with a broadband source and a fixed filter or a tunable laser or a tunable filter such as a monochromator. Step 354 is optional and involves passing the incident light through a polarizer to leave only vertically polarized light.

Step 356 symbolizes the process of detecting the incident light intensity $I_o$. Preferably this is done on the incident light side of the flow cell, but in the non "2-for-1" embodiments, it can also be one by detecting the intensity of the light transmitted through the flow cell associated with the scattered light detector.

Step 358 represents the step of shining the light on the particles in solution. This can be done using a flow cell coupled to the output of an LC column, a flow cell coupled to a capillary electrophoresis tube, a standing solution in a flow cell or any other transparent container (so long as stray light can be substantially prevented from reaching the scattered light detector) or simply using a transparent capillary electrophoresis tube.

Step 360 represents any known process for detecting the weight concentration of the particles in solution. Typically this is done by a separate flow cell in a UV absorbance detector coupled upstream or downstream of the scattering flow cell. Refractive index detectors or fluorometers may also be used in some cases.

In step 362, the scattered light intensity is detected as some selected angle between 35° and 145°. Typically this is done using a PMT but avalanche photodiodes may be used in some cases.

In step 364, the scattered light intensity $I_s$ is normalized by dividing by the incident light intensity $I_o$.

Finally, the weight averaged molecular mass $M_w$ is calculated using equation (2) in step 366.

Figure 14:
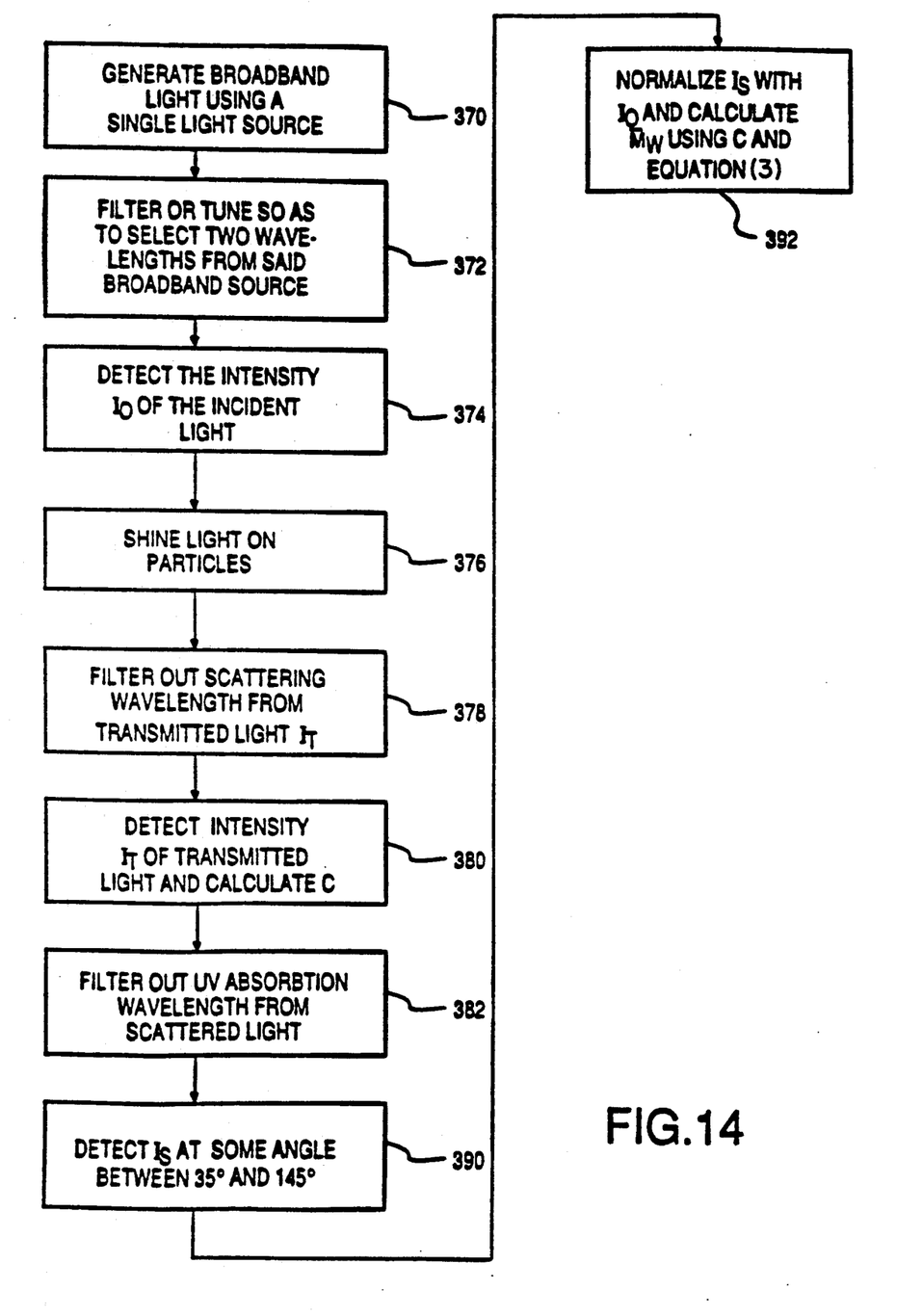
FIG. 14 is a diagram of the process for determining the weight average molecular weight using a single light source and a single flow cell.

Referring to FIG. 14, there is shown a flow chart for a method of detecting $M_w$ using a single light source and a single flow cell. Step 370 represents the process of generating light using a broadband source which outputs at least some wavelengths useful for measuring UV absorption and some wavelengths useful for scattering. Generally, this must be done with an arc source since lasers generate only one output wavelength.

Step 372 represents the process of filtering or tuning to select and pass only two wavelengths out of the light from the source. This can be done with a beam splitter and two separate fixed filters or monochromators as shown in FIG. 12 or it can be done with a single monochromator as shown in FIGS. 9 or 11. In the case of a single monochromator, the two wavelengths must be harmonics of each other. However this filtering or tuning is done, of the two wavelengths, one must be suitable for measuring UV absorption and one must be suitable for scattering. Preferably the two frequencies are individually tunable and the scattering frequency is tuned to have a wavelength where the product of the lamp output intensity versus wavelength characteristic curve and the light scattering detector efficiency versus wavelength characteristic curve is at or near a maximum.

Next, the intensity $I_o$ of the incident light is detected in step 374 by any means.

Step 376 represents shining the two frequencies on the particles of interest and can be done using any of he methods discussed above in connection with step 358 of the method of FIG. 13.

Step 378 represents the process of filtering out one of the wavelengths from the light transmitted through the solution. The wavelength eliminated is the wavelength that is used for scattered light detection. A PMT is usually used to measure the UV absorption as indicated by the intensity of the transmitted light as symbolized by step 380. This signal, after normalization using $I_o$ is used to calculate C, the weight concentration of the particles.

Step 382 represents filtering out from the scattered light at some high angle, the wavelength used for the UV absorption measurement of $I_t$.

Step 390 represents detecting the intensity $I_s$ of the scattered light at some selected high angle. This is usually done using a PMT at 90°.

Step 392 is the normalization of $I_s$ by dividing it by $I_o$ and the calculation of $M_w$ using C and equation (3).

Although the invention has been described in terms of the preferred and alternate embodiments disclosed herein, those skilled in the art will appreciate other alternative embodiments which can be made without departing from the spirit and scope of the invention. All such alternative embodiments are intended to be included within the scope of the claims appended hereto.

What is claimed is:

1. An apparatus for generating signals from which molecular weight or mass of a particle in solution can be determined, comprising:
   means for separating particles of a sample and for outputting a solution stream having said separated particles embodied therein;
   a light source;
   a filter for limiting the light from said light source to a single known wavelength which is substantially longer than the size of the particles;
   a flow cell for receiving said stream and having an input window for receiving light from said filter to illuminate said stream and having an exit window through which light scattered from said particles at high angles of approximately ninety degrees exits said flow cell;
   a scattered light detector for receiving said scattered light at high angles exiting said exit window, and having a band of maximum sensitivity and having an output at which is output an electrical signal proportional to the intensity of said scattered light;
   means for receiving at least a portion of the light from said filter incident upon said flow cell and for determining the intensity of said light and outputting an electrical signal proportional thereto;
   means for detecting the concentration of said particles in said solution and outputting a signal proportional thereto; and
   calculation means for receiving said electrical signals proportional to the scattered and incident light intensities and the weight concentration and for calculating the average molecular weight of said particles using the relationship $$I_s/I_o = BcM_w$$

where
   $I_s/I_o$ = the scattered light intensity at a high angle between 35° to 145° relative to the intensity of the incident light
   B = a predetermined optical constant which is experimentally determined for any particular optical system by measuring the scattered light intensities for at least two types of particles having known molecular weights, and C=the weight concentration of the particles in solution, and $M_w$=the weight average molecular mass.

2. The apparatus of claim 1 wherein the particle sizes are limited so as to be equal to or smaller than $\lambda°/4$ where $\lambda°$ is the wavelength light incident upon said flow 3. The apparatus of claim 1 wherein said filter filters out all wavelengths except a wavelength which is located so as to generate a maximum output signal form said scattered light detector.

4. The apparatus of claim 1 further comprising a polarizer located so as to prevent all light having other than vertical polarization from reaching said flow cell.

5. The apparatus of claim 1 wherein said flow cell has a scattering volume through which said particles flow of approximately 10 microliters.

6. The apparatus of claim 1 wherein said scattered light detector is a photomultiplier.

7. The apparatus of claim 6 wherein said photomultiplier is optimized for the blue-green wavelength and said filter filters out all wavelengths except a wavelength in the blue-green portion of the spectrum.

8. The apparatus of claim 6 wherein said photomultiplier is cooled.

9. The apparatus of claim 6 wherein said photomultiplier is a photon counting device.

10. The apparatus of claim 1 wherein said light source is a mercury arc lamp.

11. The apparatus of claim 1 wherein said light source is a Xenon arc lamp.

12. The apparatus of claim 1 wherein said light source is a laser.

13. The apparatus of claim 12 wherein said laser has blue-green output light.

14. A method of determining the average molecular weight of small particles in solution, comprising:
   separating said particles in a stream of solvent;
   passing said solvent stream through a detector capable of determining the weight concentration of said particles, determining said weight concentration and outputting a signal indicative of said weight concentration;
   passing said solvent stream through a flow cell;
   shining light having one wavelength $\lambda$ on said solvent stream flowing through said flow cell where $\lambda$ is at least four times larger than the size of said particles;
   measuring the intensity of scattered light at a selected angle between 35° and 145°;
   measuring the intensity of light incident on
   dividing said scattered light intensity by said incident light intensity;
   calculating the average molecular weight according to the relationship $$\frac{I_s}{I_o} = B C M_W$$

where
   $I_s/I_o$=the intensity of the scattered light at the selected angle;
   C=the weight concentration of said particles in said solvent stream;
   $M_w$=the average molecular weight of said particles; and
   B=a constant which can be empirically determined for each system by calibrating the system with toluene or by measuring the relative scattered light intensity for each of at least two particle samples having known average molecular weight.

15. The method of claim 14 wherein said step of separating said particles comprises the step of passing a solution containing said particles through a liquid chromatography column.

16. The method of claim 14 wherein said step of separating said particles comprises the step of separating said particles in a capillary electrophoresis apparatus.

17. The method of claim 14 wherein the step of shining one wavelength of light on said solvent stream includes the steps of generating said light with an arc lamp, filtering the output light to leave only one wavelength $\lambda$ and focussing the filtered light on said solvent stream.

18. The method of claim 17 wherein the step of measuring the intensity of scattered light includes the step of detecting the scattered light using a photomultiplier tube having a characteristic curve of sensitivity versus wavelength, and wherein said arc lamp has a characteristic curve of light output intensity versus wavelength and wherein said step of filtering said output light includes the step of filtering out substantially all wavelengths except a wavelength at or near the wavelength where the product of said characteristic curve of said arc lamp and the characteristic curve of said photomultiplier tube are a maximum.

* * * * *